United States Patent
Ibrahim et al.

(10) Patent No.: US 11,878,039 B1
(45) Date of Patent: Jan. 23, 2024

(54) COMPOSITION FOR TREATING IRRITABLE BOWEL SYNDROME

(71) Applicant: KING FAISAL UNIVERSITY, Al-Ahsa (SA)

(72) Inventors: Hairul Islam Mohamed Ibrahim, Al-Ahsa (SA); Ashraf Yassin Zaky Khalifa, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/115,933

(22) Filed: Mar. 1, 2023

(51) Int. Cl.
| | | |
|---|---|---|
| *A61K 35/741* | (2015.01) | |
| *A61P 1/00* | (2006.01) | |
| *A61K 31/59* | (2006.01) | |

(52) U.S. Cl.
CPC ............ *A61K 35/741* (2013.01); *A61K 31/59* (2013.01); *A61P 1/00* (2018.01)

(58) Field of Classification Search
None
See application file for complete search history.

(56) References Cited

U.S. PATENT DOCUMENTS

| 5,422,127 A * | 6/1995 | Dube ................... A23L 33/155 426/73 |
|---|---|---|
| 2020/0281225 A1 | 9/2020 | Kiarie et al. |
| 2023/0058302 A1* | 2/2023 | Tran ..................... A23K 10/18 |

FOREIGN PATENT DOCUMENTS

| CN | 114364388 A | | 4/2022 |
|---|---|---|---|
| GB | 2558170 A | | 7/2018 |
| KR | 20060114481 A | | 11/2006 |
| RU | 2553372 C1 | | 6/2015 |
| WO | WO 2019/2068820 | * | 10/2019 |
| WO | 2020261055 A1 | | 12/2020 |
| WO | 2021032975 A1 | | 2/2021 |
| WO | 2021252885 A1 | | 12/2021 |

OTHER PUBLICATIONS

Gonzales-Ortiz et al. Archives of Animal Nutrition, 2013, pp. 1-10.*
Jalili et al. "Effects of Vitamin D Supplementation in Patients with Irritable Bowel Syndrome: A Randomized, Double-Blind, Placebo-Controlled Clinical Trial". International Journal of Preventive Medicine, 2019, 10: 16, pp. 1-5.*
Gonzalez-Ortiz et al., "Effects of dietary supplementation of Bacillus amyloliquefaciens CECT 5940 and Enterococcus faecium CECT 4515 in adult healthy dogs," Aug. 16, 2013.

* cited by examiner

*Primary Examiner* — Vera Afremova
(74) *Attorney, Agent, or Firm* — Nath, Goldberg & Meyer; Richard C. Litman

(57) ABSTRACT

A composition for treating irritable bowel syndrome can include a mixture of *Bacillus amyloliquefaciens, Enterococcus faecium*, and Vitamin D (Calciferol). The composition can be administered to a patient to treat irritable bowel syndrome or symptoms associated with irritable bowel syndrome. For example, the composition can be used to treat colitis. The composition can include about $1\times10^6$ to $1\times10^{12}$ colony forming units (CFU) of *Bacillus amyloliquefaciens* and *Enterococcus faecium* per unit dose. In an embodiment, the composition can include at least 1 to 25 mg/L Vitamin-D.

2 Claims, 5 Drawing Sheets

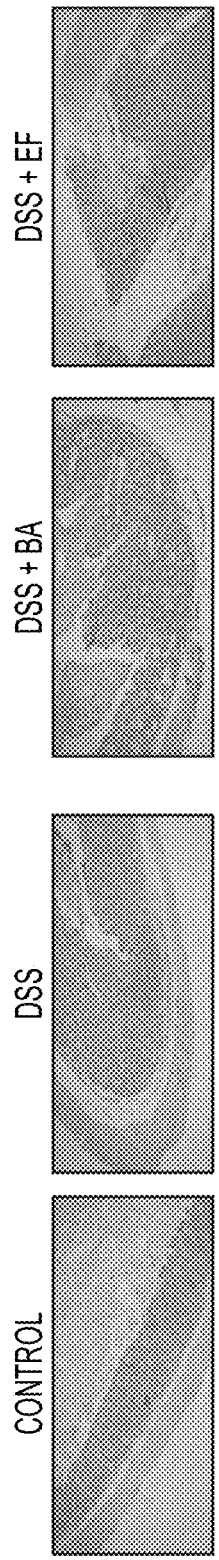
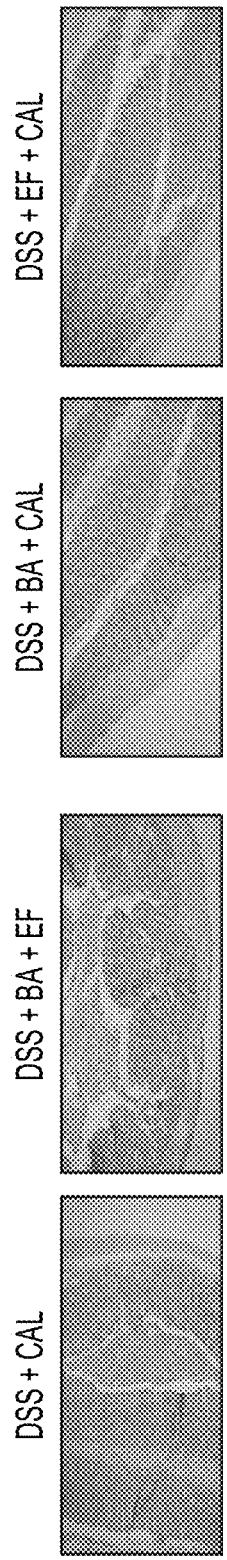
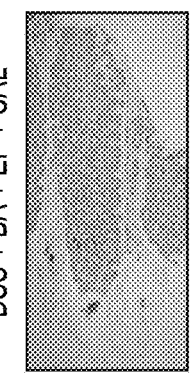

COMPOSITION FOR TREATING IRRITABLE BOWEL SYNDROME

BACKGROUND

1. Field

The disclosure of the present patent application relates to a composition for the treatment of irritable bowel syndrome and, particularly, to a composition including *Bacillus amyloliquefaciens* and *Enterococcus faecium*.

2. Description of the Related Art

Irritable Bowel Syndrome (IBS) is part of a spectrum of diseases known as functional gastrointestinal disorders which include diseases such as non-cardiac chest pain, non-ulcer dyspepsia, and chronic constipation or diarrhea. These diseases are all characterized by chronic or recurrent gastrointestinal symptoms for which no structural or biochemical cause can be found. Patients suffering from IBD and IBS share several kinds of symptoms.

Ulcerative colitis (UC) and Crohn's Disease (CD) are inflammatory bowel diseases (IBD) characterized by chronic inflammation in the intestines. UC occurs in the colon while CD may be present in the entire gastrointestinal (GI) tract. The clinical symptoms are diarrhea, abdominal pain, occasional rectal bleeding, weight loss, tiredness and sometimes fever. Although occurring at any age, IBD is most common in teenagers and young adults, which consequently may suffer from delayed development and stunted growth.

IBD is treated medically by reducing the inflammation and thereby controlling the gastrointestinal symptoms. However, a medical cure for IBD has not yet been disclosed.

Thus, a composition for treating irritable bowel syndrome solving the aforementioned problems is desired.

SUMMARY

A composition for treating irritable bowel syndrome can include a mixture of *Bacillus amyloliquefaciens*, *Enterococcus faecium*, and Vitamin D (Calciferol). The composition can be administered to a patient to treat irritable bowel syndrome or symptoms associated with irritable bowel syndrome. For example, the composition can be used to treat colitis. The composition can include about $1 \times 10^6$ to $1 \times 10^{12}$ colony forming units (CFU) of *Bacillus amyloliquefaciens* and *Enterococcus faecium* per unit dose. In an embodiment, the composition can include at least 1 to 25 mg/L Vitamin-D.

A method for treating irritable bowel syndrome can include administering a therapeutically effective amount of the composition to a patient in need thereof. The composition can include about $1 \times 10^6$ to $1 \times 10^{12}$ colony forming units (CFU) of *Bacillus amyloliquefaciens* and *Enterococcus faecium* per unit dose.

These and other features will become readily apparent upon further review of the following specification.

BRIEF DESCRIPTION OF THE DRAWINGS

FIGS. 4A-4F are microscopic images (magnification 200×) of the distal colon of the C57B16j mice when (4A) no probiotic treatment was administered; (4B) upon DSS-induction of colitis; (4C) upon administering BA to the DSS-induced mice; (4D) upon administering EF to the DSS-induced mice; (4E) upon administering calciferol to the DSS-induced mice; (4F) upon administering BA and EF to the DSS-induced mice; (4G) upon administering the BA and calciferol to the DSS-induced mice; (4H) upon administering the BA and calciferol to the DSS-induced mice upon; and (4I) upon administering the composition including BA, EF, and calciferol to the DSS-induced mice.

DETAILED DESCRIPTION OF THE PREFERRED EMBODIMENTS

Figure 1A:
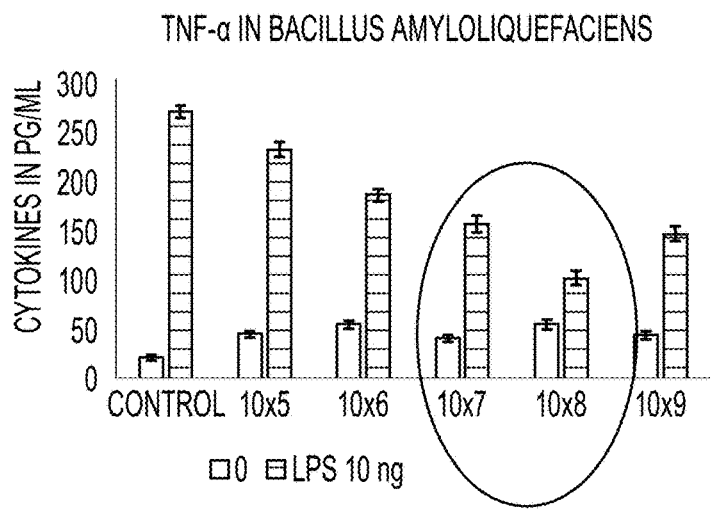
FIG. 1A is a graph showing the effect of various BA loads on cytokine (TNF-α) levels in the colonic homogenate of different mice groups in a TNBS-induced colitis model.

A composition for treating irritable bowel syndrome can include a mixture of a probiotic and Vitamin D (Calciferol). The probiotic can include at least one of *Bacillus amyloliquefaciens* (BA) and *Enterococcus faecium* (EF). The composition can be administered to a subject to treat irritable bowel syndrome or symptoms associated with irritable bowel syndrome. In an embodiment, the composition can be used to treat colitis. The composition can include about $1 \times 10^5$ to $1 \times 10^{12}$ colony forming units (CFU) of *Bacillus amyloliquefaciens* (BA) and/or *Enterococcus faecium* (EF) per unit dose. In one embodiment, the composition can include about $1 \times 10^8$ CFU of BA and/or $1 \times 10^9$ CFU of EF. In an embodiment, the composition can include about 1 mg/L to 25 mg/L of vitamin D per unit dose.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

"LPS" as used herein refers to characteristic components of the cell wall of Gram negative bacteria.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In another embodiment, the present subject matter is directed to pharmaceutical compositions comprising a therapeutically effective amount of the composition as described herein together with one or more pharmaceutically acceptable carriers, excipients, or vehicles.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. In an embodiment, the pharmaceutical composition includes the probiotic, Vitamin D and a carboxymethyl cellulose gelatin.

The present compositions can be in any suitable unit dosage form such as tablets, pills, capsules, powders, or granules, for oral administration. In an embodiment, the pharmaceutical composition is in capsule form. In an embodiment, the capsule shell is starch-based.

The present composition is typically administered at a therapeutically or pharmaceutically effective dosage, e.g., a dosage sufficient to provide treatment for irritable bowel syndrome or symptoms associated with irritable bowel syndrome. Administration of the pharmaceutical composition can be by any method that delivers the composition systemically and/or locally. These methods include oral routes, parenteral routes, intraduodenal routes, and the like.

A therapeutically effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

A method for treating irritable bowel syndrome can include administering a therapeutically effective amount of the composition to a subject in need thereof. The composition can include about $1 \times 10^5$ to $1 \times 10^{12}$ colony forming units (CFU) of *Bacillus amyloliquefaciens* and *Enterococcus faecium* per unit dose and from 1 mg/L to 25 mg/L of vitamin D per unit dose Each of BA, EF, and calciferol has demonstrated anti-inflammatory effects individually on a mammalian host system when administered alone. As described herein, however, profound synergistic effects can be achieved by administering BA, EF, and calciferol in combination as a consortium to control the bowel inflammatory syndrome. In addition, BA and EF have characteristics of obligate anaerobes, as evidenced by their abilities to ferment carbohydrate into lactic acid.

The composition for treating irritable bowel syndrome includes an optimal microbial load of BA and EF and an optimal concentration of calciferol to ameliorate or decrease colitis symptoms. In an embodiment, the composition can be particularly effective at pH levels ranging from pH 4 to pH 6. As described herein, the composition was administered orally to a DSS-induced colitis model for three weeks. After three weeks, a substantial decrease in colitis symptoms and a profound enhancement of the host gut health were achieved. Accordingly, the probiotic and Vitamin D in the composition provide a synergistic mixture of components that facilitate controlling bowel inflammatory syndrome.

The present inventors have found that, when administered in the composition, significant levels of Vitamin D were absorbed in the colon and ileum. In experiment, using an in vitro drug release method, it was further determined that increased absorption of Vitamin D was achieved by administering the composition than by administering Vitamin D alone.

In an embodiment, the composition can include about $1 \times 10^6$ to $1 \times 10^{12}$ colony forming units (CFU) of BA and EF per unit dose. The composition can include at least one strain of a probiotic. In an embodiment, the composition includes two strains of a probiotic. In an embodiment, a single dose of the composition can include at least about $1 \times 10^5$ CFU of the probiotic. In an embodiment, the composition can include about $1 \times 10^7$ CFU of the probiotic per dose or about $1 \times 10^{12}$ CFU per dose. In an embodiment, the composition can include about $1 \times 10^6$ CFU to about $1 \times 10^{10}$ CFU of the probiotic per dose. In an embodiment, the composition can include about $1 \times 10^6$ CFU to about $1 \times 10^{12}$ CFU of the probiotic per dose. In an embodiment, the composition can include probiotics in the range of from about $1 \times 10^5$ to about $1 \times 10^{10}$ colony forming units per gram of the supplement, although higher concentrations of probiotics can be supplied. In an embodiment, the composition can include about $1 \times 10^8$ CFU of BA and/or $1 \times 10^9$ CFU of EF. The composition can include from about 1 mg/L to about 25 mg/L of Vitamin D. In an embodiment, the composition can include about 3 mg/L of Vitamin D.

The present teachings are illustrated by the following examples.

Example 1

Colitis was induced in C57B16j mice by 2,4,6-trinitrobenzene sulfonic acid (TNBS). TNBS induction was made at 0 and 4 days. BA $10^8$/mL BA, EF $10^9$/mL EF, and calciferol at uM was administered as oral gavage on alternative days from day 0 to day 14.

Figure 1B:
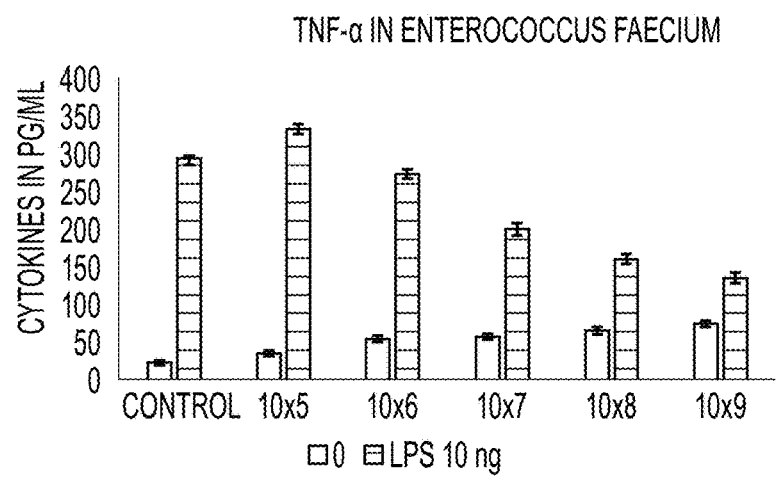
FIG. 1B is a graph showing the effect of various EF loads on cytokine (TNF-α) levels in the colonic homogenate of different mice groups in a TNBS-induced colitis model.

A comparative evaluation of cytokine (TNF-α) levels in the colonic homogenate of different mice groups from the TNBS-induced colitis model was performed. TNF-α was quantified after 14 days of the start of the experiment. All data were collected from three individual experiments and pooled and expressed as mean±SD (p<0.05). The effect of BA and EF loads on the pro-inflammatory marker (TNF-α) in TNBS-induced colitis mice is illustrated in FIGS. 1A-1B (values are expressed in pg/mL). TNBS-induced colitis mice showed elevated levels of TNF-α and treatment groups showed a remarkable decrease in TNF-α levels along with BA and EF load increase. The lowest (TNF-α) levels were achieved at bacterial loads of 10×8 for BA and 10×9 for EF, respectively.

Figure 2A:
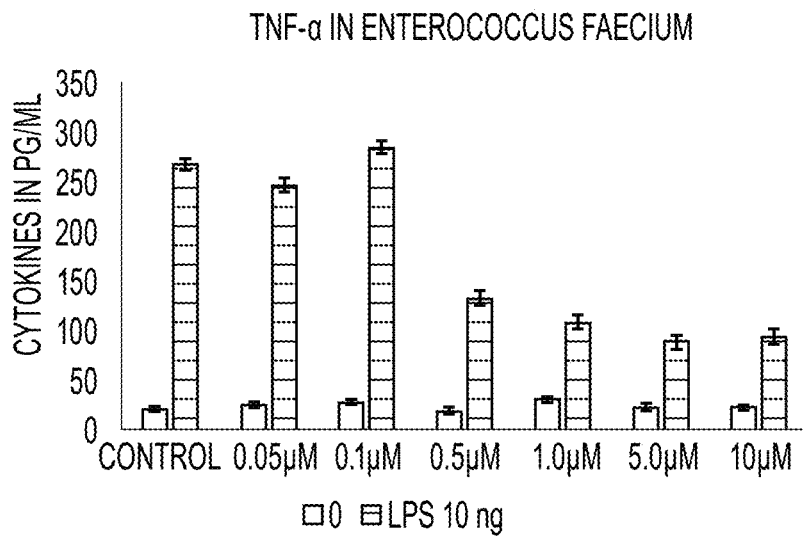
FIG. 2A is a graph showing the effect of EF on inflammation when combined with various concentrations of calciferol.
Figure 2B:
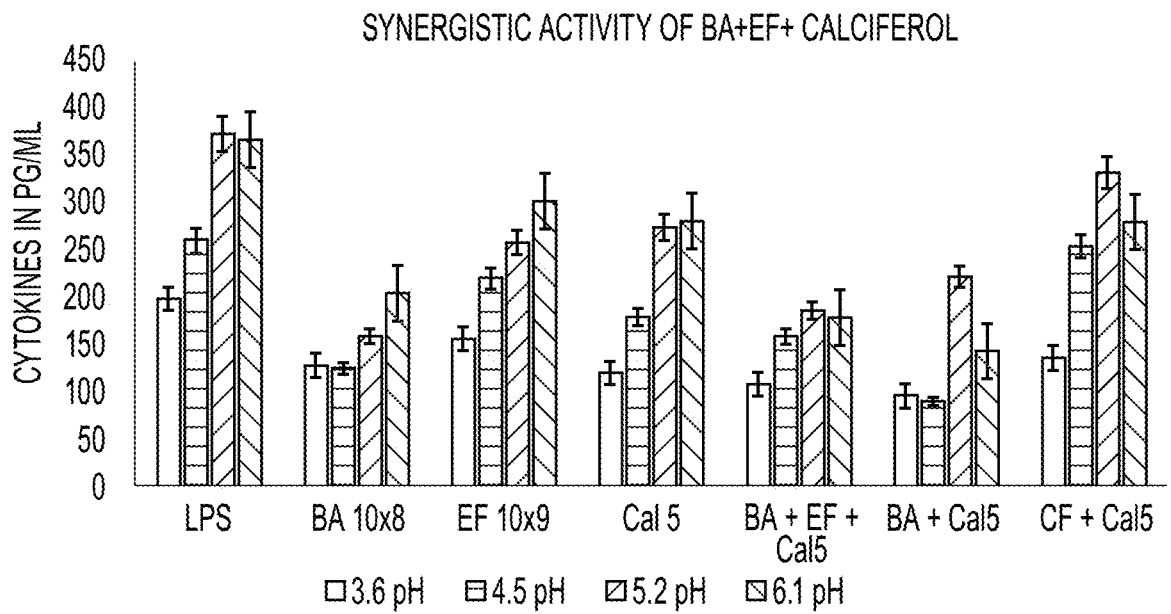
FIG. 2B is a graph showing the effect of BA, EF, calciferol at 5 uM concentration (Cal 5), and the composition including BA, EF, and calciferol on the pro inflammatory marker (TNF-α) in TNBS-induced colitis mice.

As can be seen in FIGS. 2A, EF ameliorated inflammation at calciferol concentration ranging from 0.5 uM-10 uM. FIG. 2B shows the effects of the different probiotic treatments on cytokine levels at various levels of pH. The most effective concentration of calciferol in the present composition was determined to be 5 uM at a pH value of 5.2.

Figure 3A:
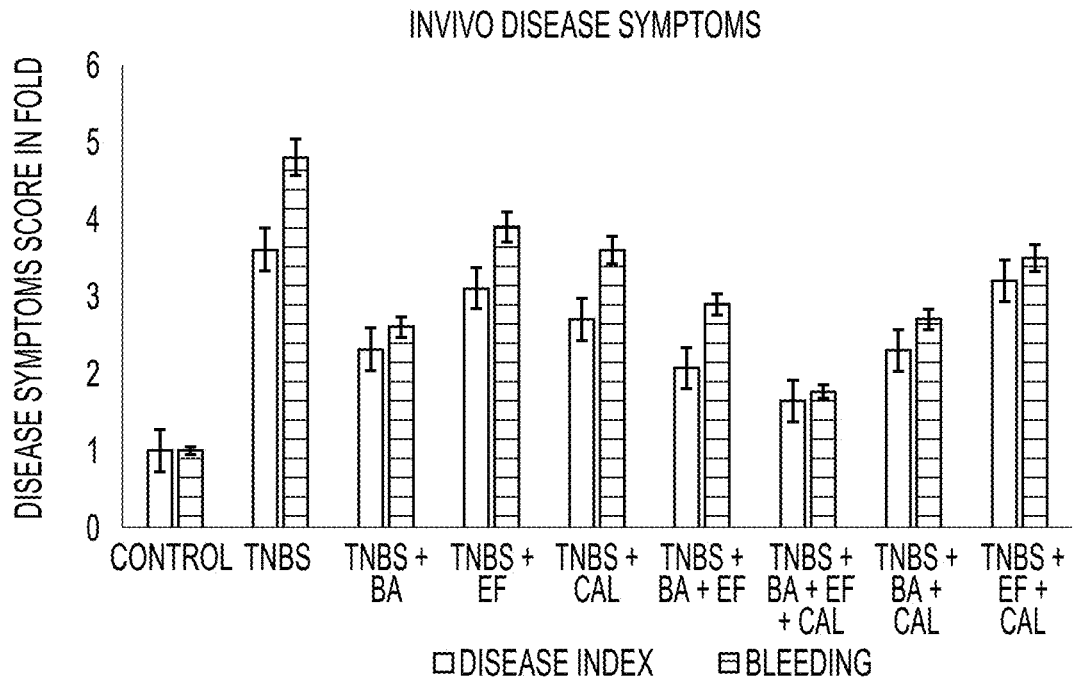
FIG. 3A is a graph showing in vivo disease symptoms in TNBS-induced colitis mice with and without probiotic treatment.
Figure 3B:
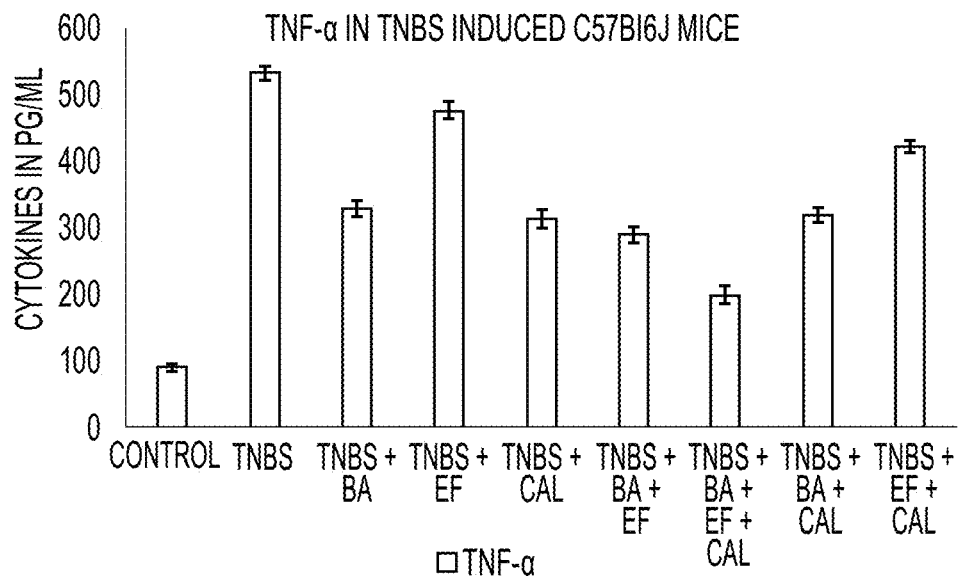
FIG. 3B is a graph showing pro inflammatory marker (TNF-α) levels in TNBS-induced colitis mice with and without probiotic treatment.

FIG. 3A shows synergistic effects of the composition including BA and EF and Vitamin D on in vivo disease symptoms in TNBS-induced colitis mice. Disease index and bleeding indicated degree of recovery of the disease in the group treated with the composition. FIG. 3B demonstrated synergistic effects of the composition including BA and EF and Vitamin D on the pro-inflammatory marker (TNF-α) over the pH range 3.6-6.1 in TNBS-induced colitis mice. TNF-α was quantified after 14 days of the experiment. The values are expressed in pg/mL. All data were collected from three individual experiments and pooled and expressed as mean±SD (p<0.05). *p<0.05 represents significance.

Figure 5A:
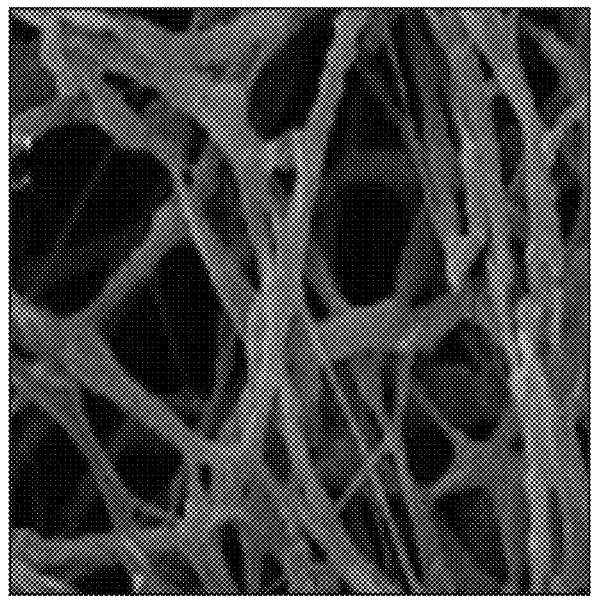
FIG. 5A is a scanning electron micrograph (SEM) of BA.
Figure 5B:
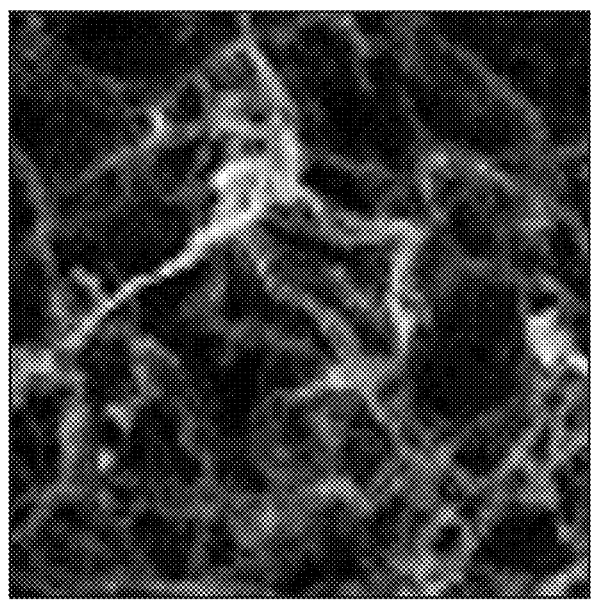
FIG. 5B is a scanning electron micrograph (SEM) of the composition including BA, EF, and calciferol at pH 5.2.

Microscopic examination of the distal colon of the C57B16j mice with DSS-induced colitis was carried out. Cellular infiltration and inflammation were observed. The pathological changes of treatment were observed using the H&E staining method. As shown in the microscopic images depicted in FIGS. 4A-4I (magnification 200×) the composition including BA, EF, and calciferol significantly alleviated DSS-induced colitis in C57B16j mice. All of the data were collected from three individual experiments and pooled and expressed as mean±SD (p<0.05). *p<0.05 represents significance compared to the DSS vs. DSS+BA+EF+Calciferol group. FIGS. 5A-5B depict scanning electron micrograph of BA; and the composition including BA, EF, and calciferol (vitamin D) at pH 5.2, respectively. The image was obtained at 10000×. The vitamin D coupling with BA modified the cell membrane and such modifications revealed the antigenic variation as compared with BA alone.

It is to be understood that the composition for treating irritable bowel syndrome is not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for treating irritable bowel syndrome comprising administering a therapeutically effective amount of a composition to a subject in need thereof, the composition comprising:
    a probiotic comprising $1 \times 10^8$ colony forming units of *Bacillus amyloliquefaciens* (BA) and $1 \times 10^9$ colony forming units of *Enterococcus faecium* (EF); and
    from 0.5 uM-10 uM of Vitamin D,
    wherein the composition is administered to the subject at a pH of 3.6 to 6.1.

2. The method for treating irritable bowel syndrome as recited in claim 1, wherein the composition has a pH ranging from 4 to 6.

* * * * *